(12) United States Patent
Ohshima et al.

(10) Patent No.: US 7,643,139 B2
(45) Date of Patent: Jan. 5, 2010

(54) METHOD AND APPARATUS FOR DETECTING DEFECTS

(75) Inventors: Yoshimasa Ohshima, Yokohama (JP); Minori Noguchi, Mitsukaido (JP); Hiroyuki Nakano, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 175 days.

(21) Appl. No.: 11/206,209

(22) Filed: Aug. 18, 2005

(65) Prior Publication Data

US 2006/0068512 A1 Mar. 30, 2006

(30) Foreign Application Priority Data

Sep. 29, 2004 (JP) ............... 2004-283014

(51) Int. Cl.
*G01N 21/00* (2006.01)
(52) U.S. Cl. .................. 356/237.4; 356/237.5
(58) Field of Classification Search .... 356/237.1–237.5
See application file for complete search history.

(56) References Cited

U.S. PATENT DOCUMENTS

| 4,601,576 A | 7/1986 | Galbraith | |
|---|---|---|---|
| 5,798,829 A | 8/1998 | Vaez-Iravani | |
| 5,801,824 A * | 9/1998 | Henley | 356/237.2 |
| 6,226,079 B1 * | 5/2001 | Takeda et al. | 356/237.2 |
| 6,411,377 B1 * | 6/2002 | Noguchi et al. | 356/237.4 |
| 7,218,392 B2 | 5/2007 | Biellak et al. | |
| 7,426,023 B2 * | 9/2008 | Ohshima et al. | 356/237.2 |
| 2002/0021438 A1 * | 2/2002 | Isozaki et al. | 356/237.5 |
| 2002/0088952 A1 * | 7/2002 | Rao et al. | 250/559.45 |

FOREIGN PATENT DOCUMENTS

| JP | 06-102189 | 4/1994 |
|---|---|---|
| JP | 2001-281162 | 10/2001 |
| JP | 2004-531735 A | 1/2003 |
| JP | 2003-247940 A | 5/2003 |
| JP | 2003-166947 | 6/2003 |
| JP | 2004-531735 T | 10/2004 |

* cited by examiner

*Primary Examiner*—Hoa Q Pham
(74) *Attorney, Agent, or Firm*—Antonelli, Terry, Stout & Kraus, LLP.

(57) ABSTRACT

An inspection apparatus projects a laser beam on the surface of a SOI wafer and detects foreign matter on and defects in the surface of the SOI wafer by receiving scattered light reflected from the surface of the SOI wafer. The wavelength of the laser beam used by the inspection apparatus is determined so that a penetration depth of the laser beam in a Si thin film may be 10 nm or below to detect only foreign matter on and defects in the outermost surface and not to detect foreign matter and defects in a BOX layer. Only the foreign matter on and defects in the outermost surface layer can be detected without being influenced by thin-film interference by projecting the laser beam on the surface of the SOI wafer and receiving scattered light rays.

6 Claims, 7 Drawing Sheets

Reflectance of the surface of Si layer

● : Defect 1
× : Defect 2

METHOD AND APPARATUS FOR DETECTING DEFECTS

BACKGROUND OF THE INVENTION

The present invention relates to a method of sensitively and quickly detecting minute defects in semiconductor substrates or the like and an apparatus for carrying out the method.

A production line for producing semiconductor substrates or thin-film substrates typically includes the inspection of semiconductor substrates or thin-film substrates for foreign that may be adhering to the surfaces of semiconductor substrates or thin-film substrates so as to monitor the dust producing condition of the manufacturing equipment. For example, minute foreign matter of 0.1 µm or below that is adhering to a surface of a semiconductor substrate needs to be detected before forming a circuit pattern on the surface of the semiconductor substrate. Techniques for detecting minute defects on a sample semiconductor substrate, as disclosed in U.S. Pat. Nos. 4,601,576 and 5,798,829, involve the scanning of the entire surface of the sample semiconductor substrate with a laser beam of several tens of micrometers in diameter by turning and translating the sample semiconductor substrate, and light scattered by foreign matter and defects is detected to inspect the surface of the semiconductor substrate for foreign matter and defects.

In a SOI wafer (silicon-on-insulator wafer), a BOX layer (oxide film) and a SOI layer (Si), each having a thickness in the range of several tens of nanometers to several hundreds of nanometers, are formed in layers on a bulk Si. Therefore, the intensity of scattered light that have been scattered by foreign matter and defects varies according to the thickness of the BOX layer and the SOI layer due to the influence of thin-film interference. A method disclosed in JP-A No. 6-102189 uses an illumination angle that makes the intensity of light reflected in a regular reflection mode maximum to avoid the variation of detection sensitivity due to the influence of thin-film interference. This known method, however, can not deal with an intralayer thickness variation. Methods disclosed in JP-A Nos. 2001-281162 and 2003-166947 use light of a plurality of wavelengths for illumination to reduce the influence of thin-film interference.

SUMMARY OF THE INVENTION

The present invention provides an inspection apparatus for inspecting a surface of a SOI wafer for foreign matter on and defects in the surface of the SOI wafer by irradiating the surface of the SOI wafer with a laser beam and receiving light that has been scattered by the surface of the SOI wafer. The inspection apparatus is capable of achieving inspection without being affected by a variation of the thickness of a BOX layer and a SOI layer formed on the SOI wafer, does not detect foreign matter and defects in the BOX layer and is capable of detecting only foreign matter and defects on a surface of the SOI wafer.

The inventors of the present invention have found through studies that the optical characteristics, namely, the refractive index n and absorption coefficient k, of Si are dependent on the wavelength of a laser beam used for irradiating the SOI wafer, and that the penetration depth, i.e., distance at which the intensity is attenuated by a factor of 1/e, which is calculated by using the refractive index and the absorption coefficient, decreases for light of a wavelength in a wavelength range. When a laser beam having a wavelength in such a wavelength range is used for irradiation, only foreign matter and defects on a surface of a SOI wafer can be detected without being affected by the variation of the thickness of a BOX layer and a SOI layer formed on the SOI wafer.

According to the present invention, inspection can be achieved without being affected by thin-film interference, and, hence, it is possible to detect only that foreign matter and those defects which are present on a surface of a SOI wafer with stable sensitivity.

These and other objects, features and advantages of the present invention will be apparent from the following more particular description of preferred embodiments of the invention, as illustrated in the accompanying drawings.

DESCRIPTION OF THE PREFERRED EMBODIMENTS

Preferred embodiments of the present invention will be described.

Figure 1:
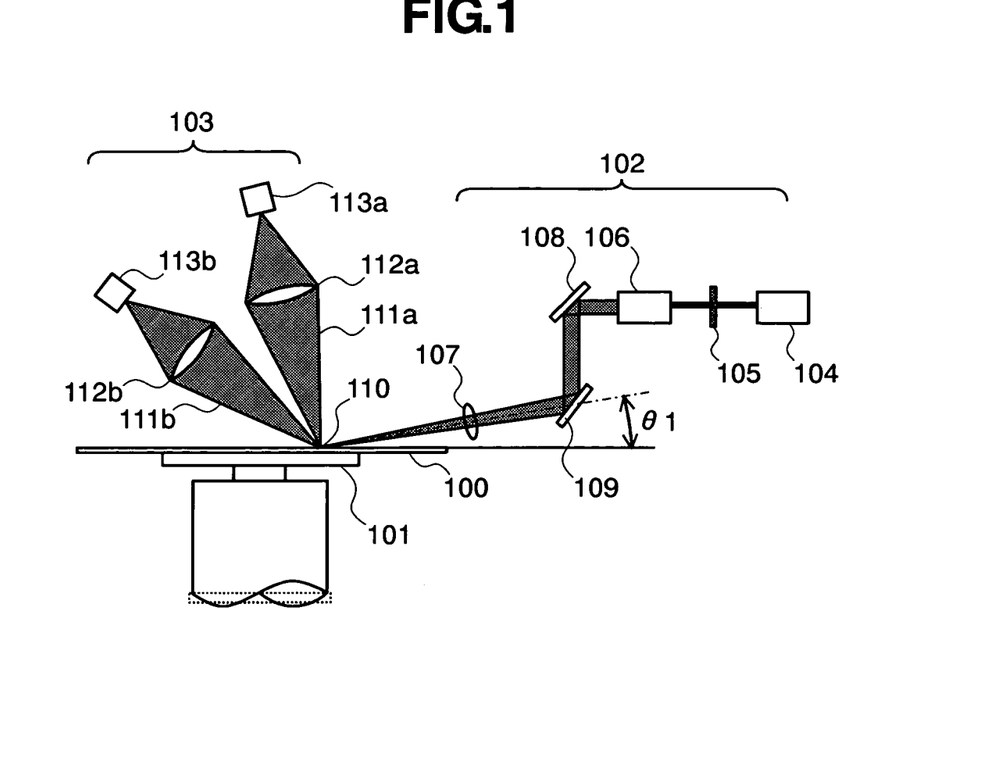
FIG. 1 is a schematic diagram of an inspection apparatus representing a preferred embodiment according to the present invention.

FIG. 1 shows an inspection apparatus which represents a preferred embodiment according to the present invention for inspecting a semiconductor wafer for foreign matter adhering thereto. The inspection apparatus includes, as principal components, a wafer stage 101, an illuminating optical system 102 and a detecting optical system 103. The illuminating optical system 102 includes a laser 104, such as an Ar laser or a semiconductor laser, a wave plate 105, a beam expander 106 and a condenser lens 107. The wave plate 105 adjusts the direction of polarization of a laser beam emitted by the laser 104 to an optional direction. The beam expander 106 increases the diameter of the laser beam. The laser beam gathered by the condenser lens 107 is projected on a wafer 100 to illuminate a detection area 110 on a wafer 100. Mirrors 108 and 109 are used, when necessary, to change the optical path of the laser beam.

The detecting optical system 103 has a high-angle detection system, including a scattered light detecting lens 112a and a photoelectric transducer 113a, and a low-angle detection system, including a scattered light detecting lens 112b and a photoelectric transducer 113b. The high-angle and the low-angle detection systems receive scattered light rays 111a and 111b, respectively, that have been scattered by foreign matter and defects in the detection area. The high-angle and the low-angle detection systems execute optical processing of the scattered light rays 111a and 111b, such as changing and adjusting the optical characteristics of the scattered light rays by using polarizing plates and spatial filters. Each of the photoelectric transducers 113a and 113b generates an electrical signal that is proportional to the intensity of the scattered light rays directed thereto. A signal processing circuit, not shown, processes the signals generated by the photoelectric transducers 113a and 113b to detect foreign matter and defects and to determine the sizes of the foreign matter and the defects. The photoelectric transducers 113a and 113b included in the detecting optical system 103 are TV cameras, linear CCDs, TDI sensors or photomultipliers.

Foreign matter and defects can be separately detected by detecting the scattered light rays by use of the high-angle and the low-angle detection systems, operating on the detection signals provided by the high-angle and the low-angle detection systems and comparing the results of such operations. The foreign matter adhering to the surface of the wafer typically have convex shapes, while the defects have concave shapes. Therefore, the intensity of light rays that have been scattered by convex foreign matter and have been received by the high-angle detection system and the intensity of light rays scattered by the convex foreign matter and received by the low-angle detection system are approximately equal to each other; and, hence, the respective levels of detection signals provided by the high-angle and the low-angle detection systems in connection with convex foreign matter are substantially the same. Whereas, the intensity of light rays scattered by concave defects and received by the high-angle detection system and the intensity of light rays scattered by the concave defects and received by the low-angle detection system are different; and, hence, in this case, the respective levels of detection signals provided by the high-angle and the low-angle detection systems are different. Thus, the foreign matter and the defects can be separately detected by using the intensity difference, i.e. by operating on detection signals provided by the high-angle and the low-angle detection systems and comparing the results of this operation.

The wafer stage 101 includes a chuck, not shown, for holding the wafer 100, a rotating mechanism, not shown, for rotating the wafer 100, and a translating mechanism, not shown, for translating the wafer 100 in a radial direction. Foreign matter and defects on the entire surface of the wafer 100 can be detected and the sizes of the same can be measured by rotating and translating the wafer 100 in a horizontal plane by use of the wafer stage 101.

Figure 2:
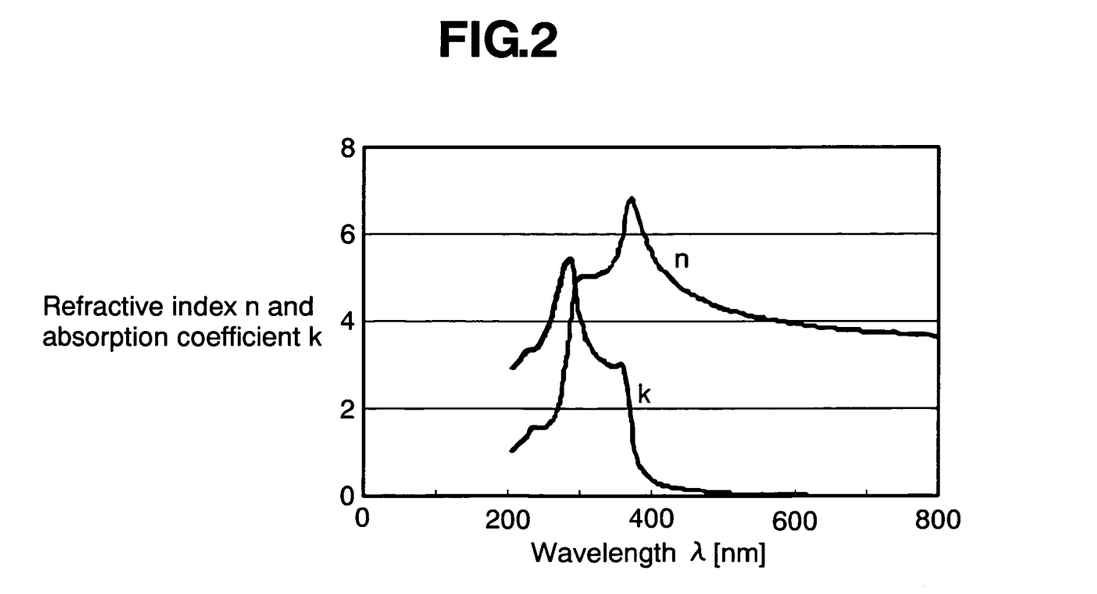
FIG. 2 is a graph showing optical characteristics of Si.

The wavelength of the laser beam for illuminating the surface of the wafer 100 will be studied. As obvious from FIG. 2, the optical characteristics, namely, the refractive index n and the absorption coefficient k, of Si are dependent on the wavelength of the laser beam that is used for irradiating the wafer 100 (refer to E. D. Palik (Naval Research Laboratory), "Handbook of Optical Constants of Solids, Silicon", p. 552 (1985)). The penetration depth d (distance at which the intensity is attenuated by a factor of 1/e) can be calculated by using Expression (1), $$d = \frac{\lambda}{2\pi nk} \quad (1)$$

where λ is the wavelength of the laser beam, n is the refractive index of Si and k is the absorption coefficient of Si (Kubota, "Hadou Kogaku, Denji Hadou", Iwanami Shoten, p. 15 (1971)).

Figure 3:
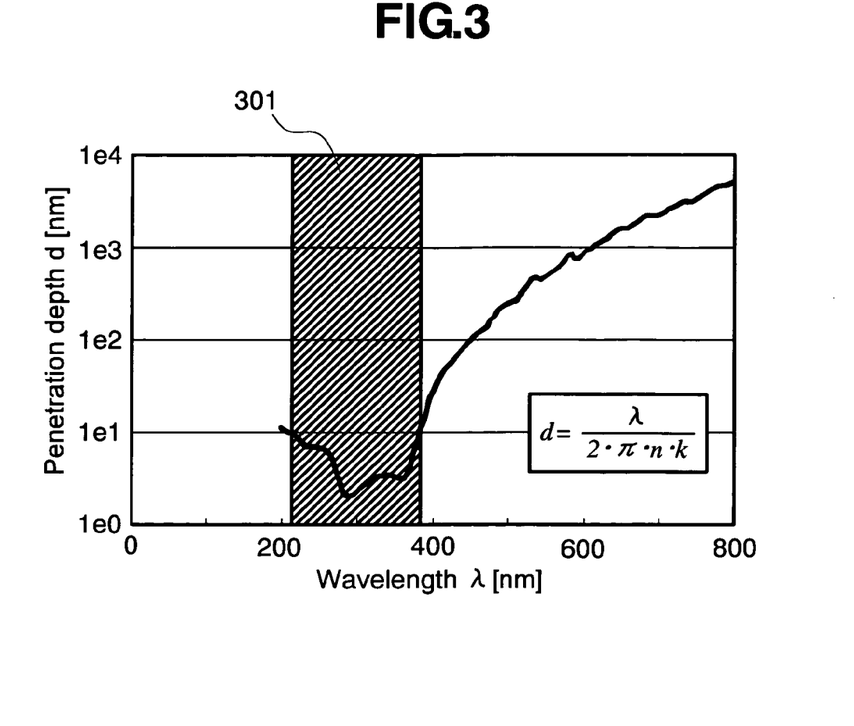
FIG. 3 is a graph showing the variation of penetration depth into a Si wafer versus wavelength.

It has been found through experiments that the penetration depth is shallower than 10 nm, corresponding to 1e1 in FIG. 3, when the wavelength of the laser beam is in the shaded wavelength range 301 of 210 to 390 nm. When the laser beam which has a wavelength in the wavelength range 301 is used for illumination, the laser beam does not reach a BOX layer, and, hence, thin-film interference does not occur.

Figure 4:
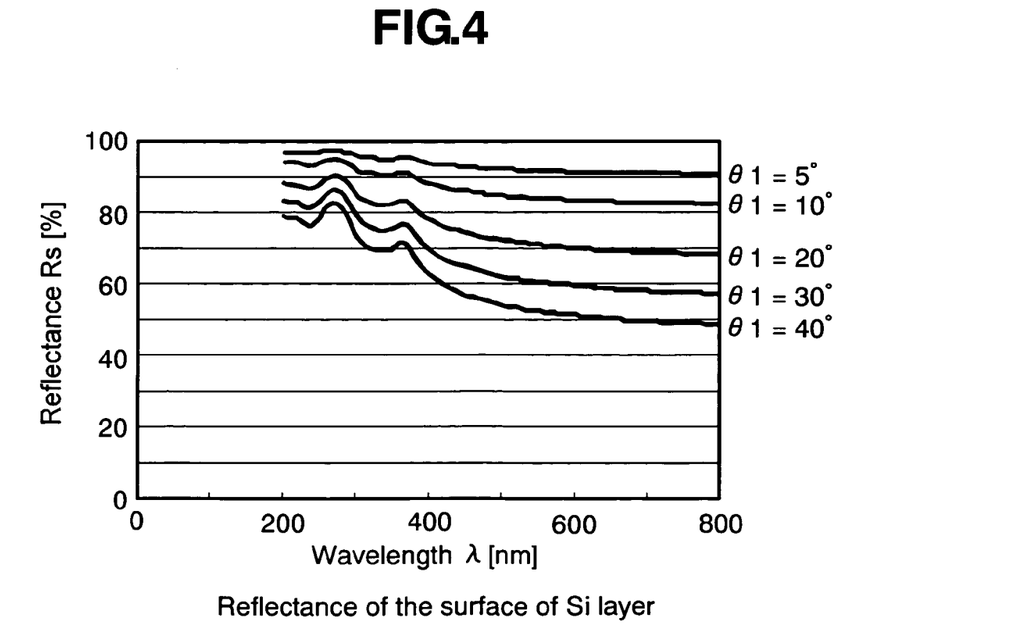
FIG. 4 is a graph showing the variation of reflectance of a surface of a Si wafer versus wavelength for different angles of an irradiating laser beam relative to the surface of a Si wafer.

The illuminating angle θ1 shown in FIG. 1 will be studied. Reflectance for an illuminating angle can be calculated by using the refractive index and absorption coefficient. FIG. 4 shows calculated data for s-polarized light. When the illuminating angle is 30° or below, the reflectance is 70% or above. Considering the construction of the inspection apparatus, it is desirable when the illuminating angle is in the range of 30 to 30°.

Figure 5:
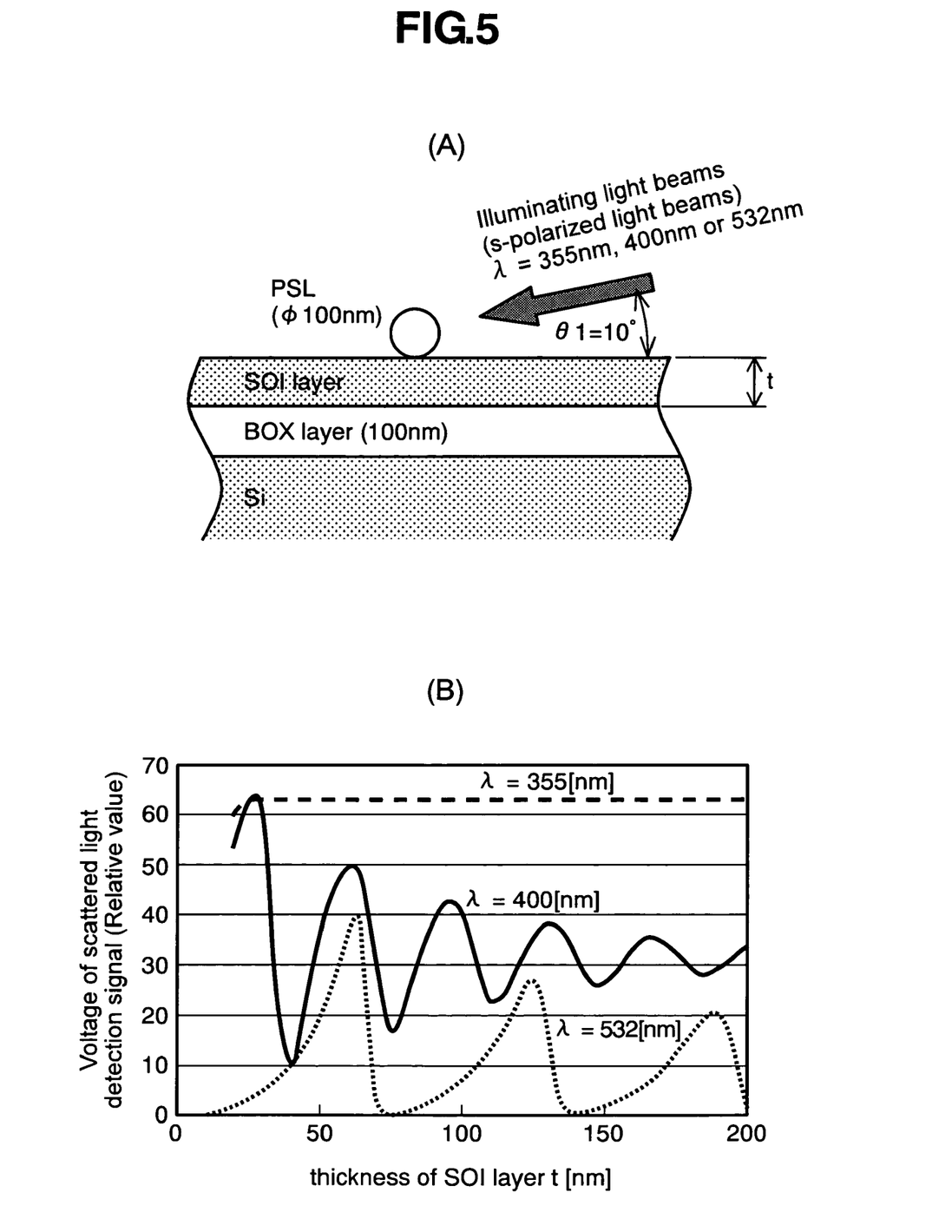
FIG. 5A is a diagrammatic sectional view which illustrates the relation between a standard particle and an irradiating light beam.
FIG. 5B is a graph showing the dependence of the relation between the thickness of a SOI layer and a scattered light detection voltage on the wavelength of an irradiating light beam.

The effect of wavelength range and illuminating angle has been by simulation using, for example, EM Filex (Weidlinger Associates, USA). FIGS. 5A and 5B show the results of such simulation. The thickness of the BOX layer was 100 nm. A simulation was performed for different thicknesses of the SOI layer in the range of 20 to 200 nm.

As shown in FIG. 5A, a standard particle of a polystyrene latex was placed on the SOI layer, and the surface of the SOI layer was illuminated with s-polarized light at an illuminating angle of 10°. The simulation used s-polarized light having a wavelength of 355 nm within a wavelength range of light whose penetration depth is 10 nm or below, and s-polarized light having wavelengths of 400 nm and 532 nm was used outside the same wavelength range. As shown in FIG. 5B, the level of scattered light detection signals, namely, voltages, are seen to vary according to the variation of the thickness of the SOI layer, when the s-polarized light having wavelengths of 400 nm and 532 nm was used, due to the effect of thin-film interference. The voltage representing a scattered light detection signal was not affected by the effect of the thin-film interference, and the voltage was stable regardless of the variation of the thickness of the SOI layer when s-polarized light having a wavelength of 355 nm, whose penetration depth is 10 nm or below, was used. The level of the detection signal provided when the s-polarized light of 355 nm was higher than those of the detection signals provided when the s-polarized light of 400 nm and 532 nm was used. The simulation proved that sensitive inspection can be achieved by using s-polarized light of 355 nm. Since the penetration depth of s-polarized light of 355 nm is shallow, the effect of the same s-polarized light is the same for the inspection of bare Si wafers. Thus, the sensitivity of inspection using s-polarized light of 355 nm is higher than the sensitivity of inspection using s-polarized light having wavelengths other than 355 nm.

As apparent from the foregoing description, interference between reflected light rays reflected by the opposite surfaces of an optically transparent thin film formed on a surface of a wafer can be prevented and defects in the surface of the wafer can be stably detected with high accuracy by using the illuminating optical system of the present invention.

Figure 6:
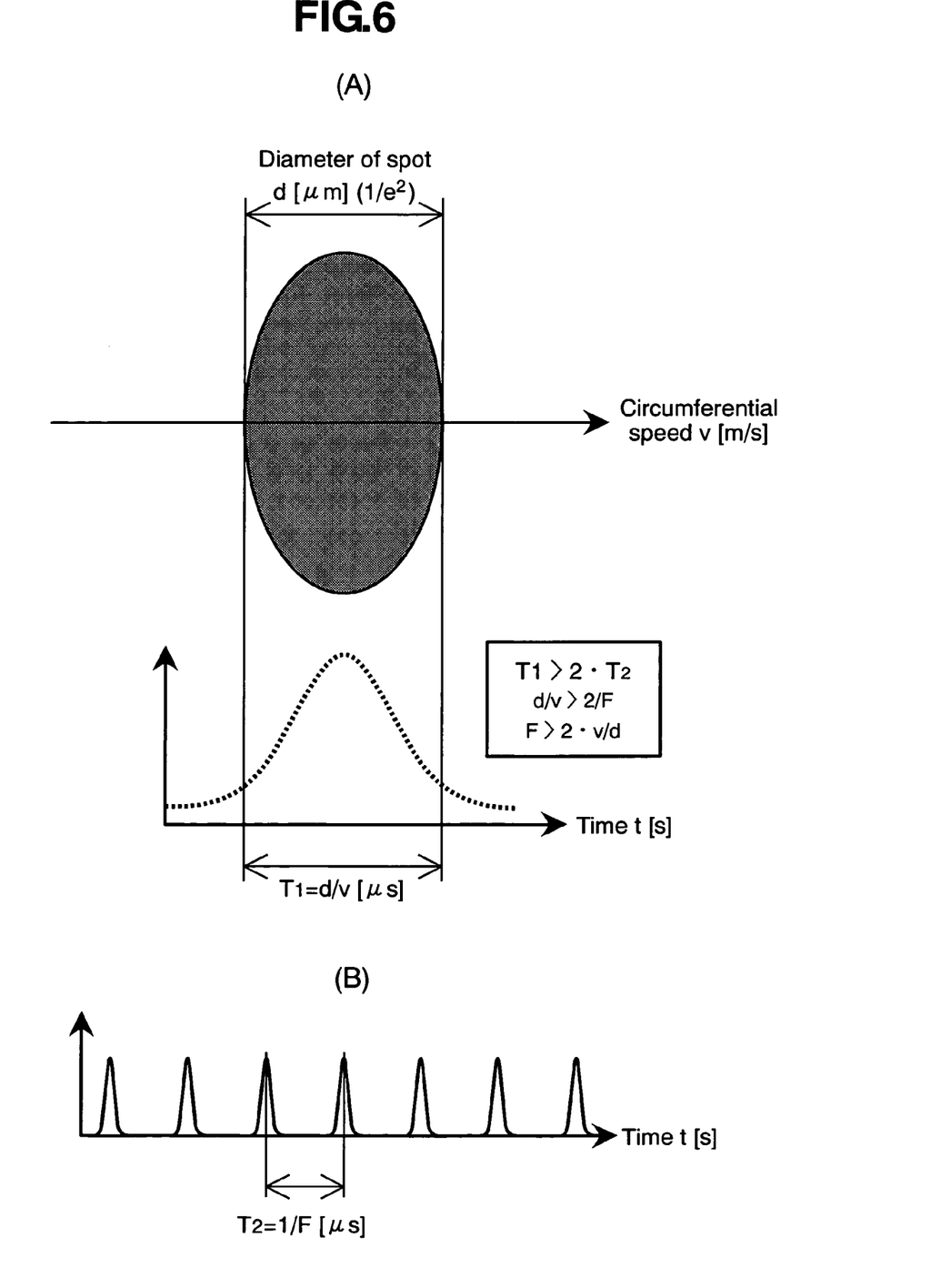
FIG. 6A is a diagrammatic view of a spot formed by a laser beam on a wafer along with a graphical representation of the intensity distribution thereof.
FIG. 6B is a diagram showing the output of a pulsed laser with time.

Although it is not necessary to take any measures when the laser oscillates continuously, when the laser emits pulsed light, the relation of the frequency of oscillation of the laser to the diameter of the laser beam and the moving speed of foreign matter and defects that move as the wafer rotates must be taken into consideration. FIGS. 6A and 6B illustrate this relation. Referring to FIG. 6A, when the diameter of a spot formed by the laser beam on a wafer is d ($1/e^2$) (μm), the circumferential speed of foreign matter and defects moving as the wafer rotates is v (m/s) and the oscillation frequency of the laser is F (MHz), the time T1 (μs) in which foreign matter and defects of infinitesimal sizes cross the spot of the laser beam, i.e., the duration of reflection of scattered light, is expressed by:

$$T1 = d/v \quad (2)$$

As shown in FIG. 6B, $$T2 = 1/F \quad (3)$$

where T2 (μs) is the period of pulses of the pulsed laser beam.

From a sampling theorem, $$T1 > 2 \times T2 \quad (4)$$

From Expressions (2), (3) and (4), $$F > 2 \times v/d \quad (5)$$

Normally, the oscillation frequency F of the laser and the diameter d of the spot of the laser beam are fixed. The circumferential speed v is determined so as to meet a condition expressed by Expression (5). Thus, the rotating speed N (rps) of a wafer having a diameter R (m) needs to meet a condition expressed by Expression (6).

$$N < d \cdot F/(4 \cdot \Pi \cdot R) \quad (6)$$

Figure 7:
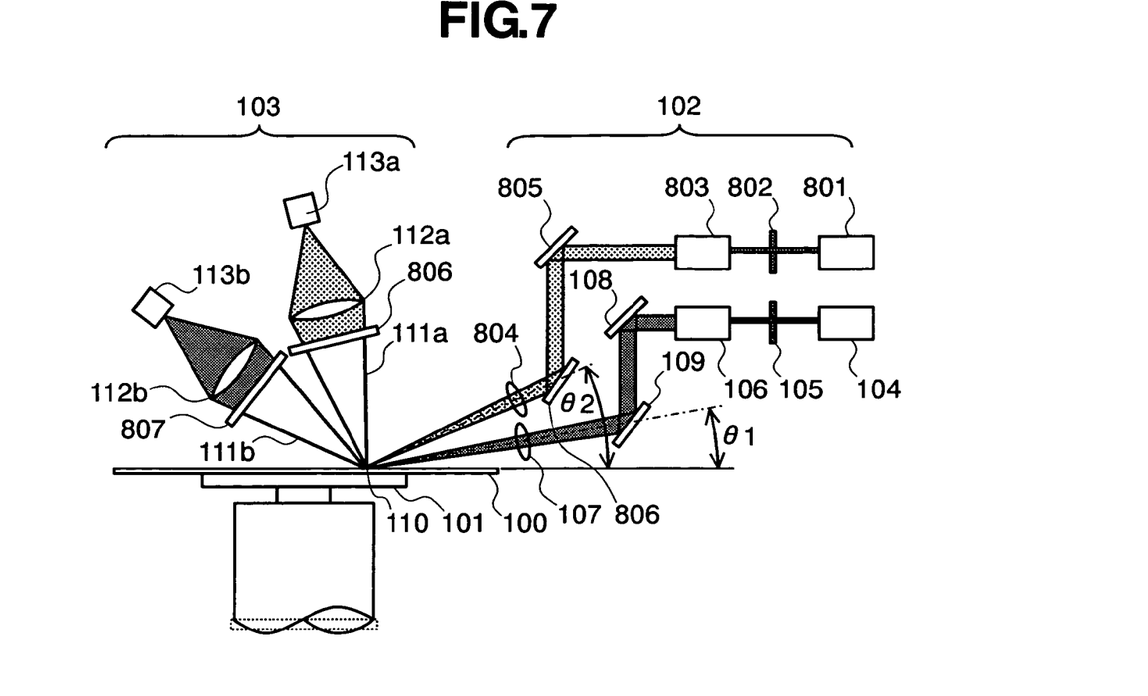
FIG. 7 is a schematic diagram of an inspection apparatus that projects a light beam at two different irradiation angles and detects scattered light.

FIG. 7 shows an inspection apparatus representing another embodiment according to the present invention. Convex defects and concave defects can be discriminated from each other by illuminating the surface of a wafer in different illuminating modes, respectively, using different illuminating angles, as shown in FIG. 7, detecting scattered light rays that have been scattered when the surface of the wafer was illuminated in the different illuminating modes and comparing detection voltages that have been generated, respectively, when the surface of the wafer is illuminated in the different illuminating modes. A first illuminating optical system, including a laser 104, a wave plate 105, a beam expander 106, mirrors 108 and 109 and a condenser lens 107, is the same as the illuminating optical system shown in FIG. 1. The first illuminating optical system illuminates a surface of a wafer with a laser beam having a wavelength of $\lambda 1$ at an illuminating angle of $\theta 1$. A second illuminating optical system includes a laser 801, a wave plate 802, a beam expander 803, mirrors 805 and 806 and a condenser lens 804. The first and the second illuminating optical system are the same in construction. The second illuminating optical system illuminates the surface of the wafer with a laser beam having a wavelength of $\lambda 2$ at an illuminating angle of $\theta 2$. The detecting optical system shown in FIG. 7 is the same as that shown in FIG. 1, except that the former includes optical wavelength filters 806 and 807. The optical wavelength filter 807 transmits light having a wavelength of $\lambda 1$ and absorbs light having a wavelength of $\lambda 2$. The optical wavelength filter 806 transmits light having a wavelength of $\lambda 2$ and absorbs light having a wavelength of $\lambda 1$. Thus, scattered light rays respectively having different wavelengths and which separately travel through scattered light condensing lenses 112a and 112b can be individually detected by photoelectric transducers 113a and 113b, respectively. When light beams of different wavelengths are used for detecting different types of defects, logical OR processing between signals provided by the two photoelectric transducers 113a and 113b may be used. The wavelengths $\lambda 1$ and $\lambda 2$ are those that make the penetration depth 10 nm or below.

Figure 8:
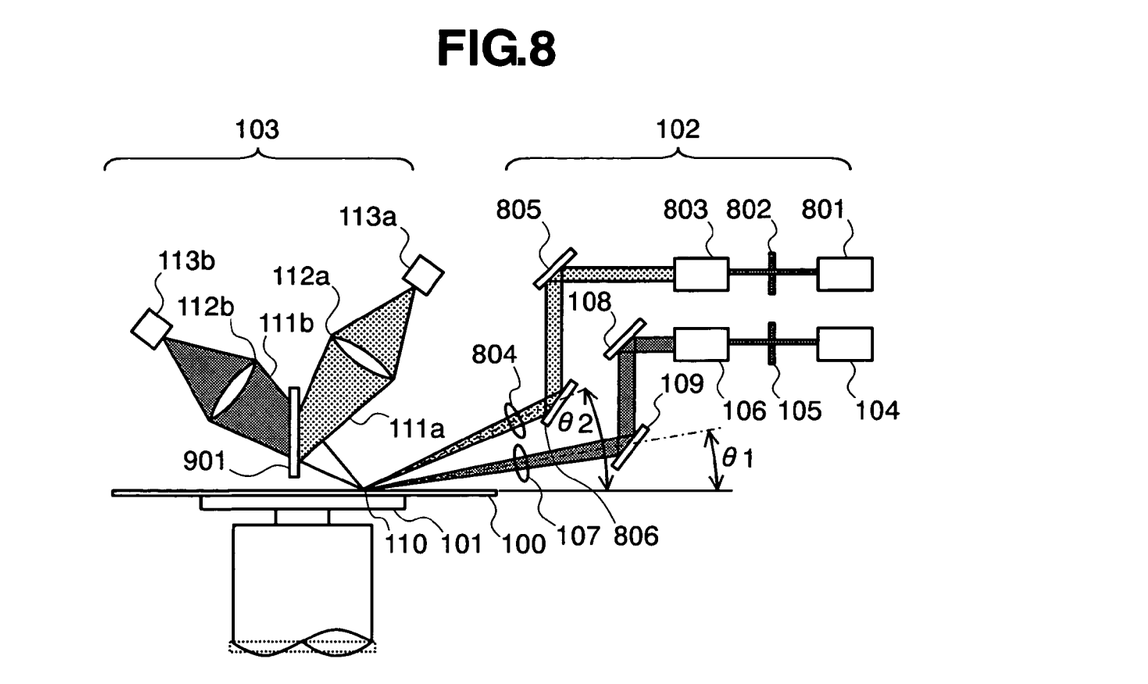
FIG. 8 is a schematic diagram of an inspection apparatus that projects light beams respectively having different wavelengths from the same direction and detects scattered light.

FIG. 8 shows an inspection apparatus in representing a third embodiment according to the present invention that is capable of individually detecting scattered light lays of two different wavelengths similar to the inspection apparatus shown in FIG. 7. As shown in FIG. 8, the detecting optical system 103 provided in the inspection apparatus shown in FIG. 8 includes a dichroic mirror 901 that transmits light having a wavelength of $\lambda 1$ and reflects light having a wavelength of $\lambda 2$. The inspection apparatus detects transmitted scattered light rays and reflected scattered light rays separately to produce the same effect as that of the inspection apparatus shown in FIG. 7.

Figure 9:
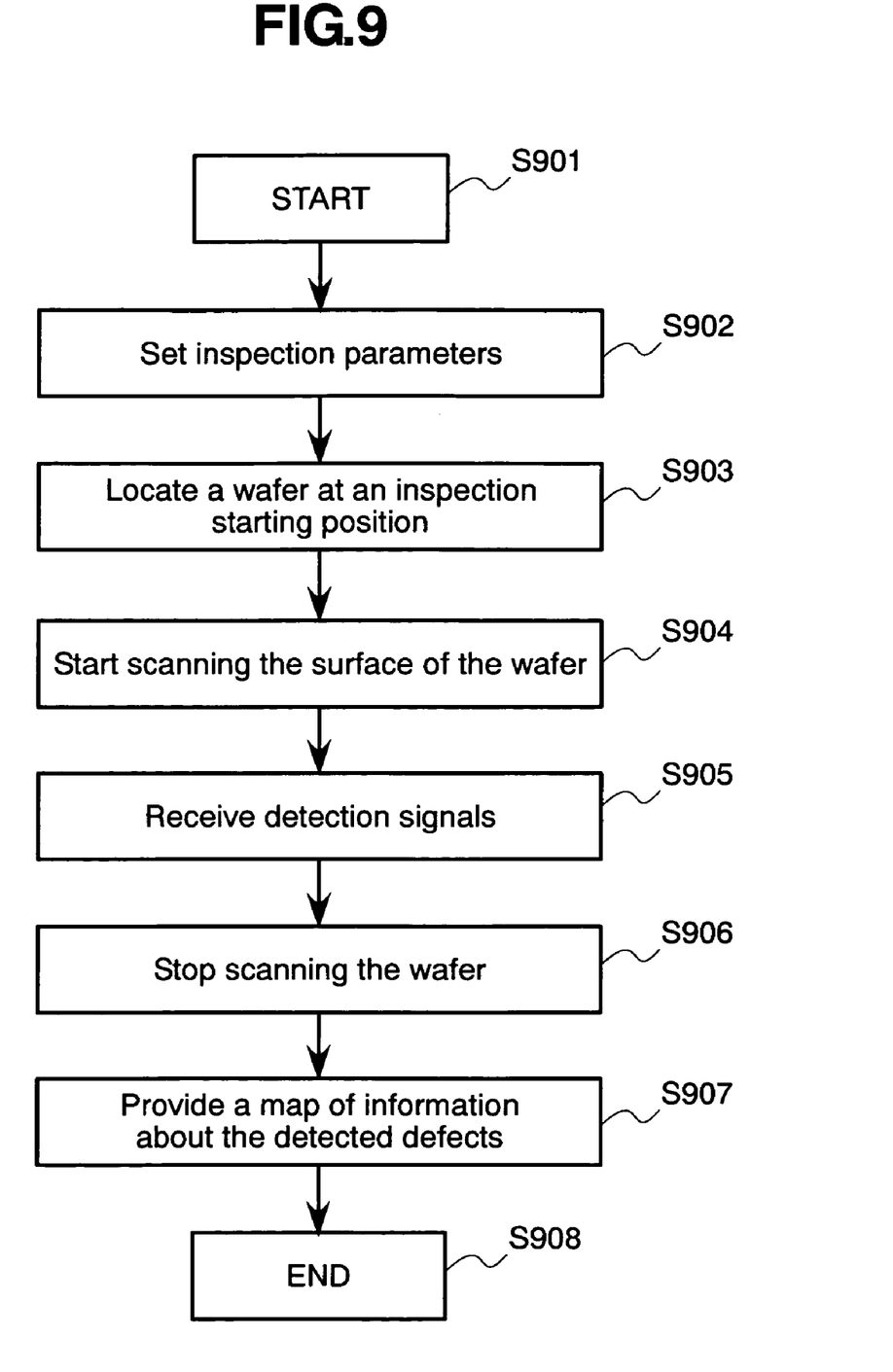
FIG. 9 is a flow chart of an inspection procedure.

FIG. 9 is a flow chart of an inspection procedure. Referring to FIG. 9, an inspecting operation included in an inspection procedure is started in step S901. Parameters of inspection, such as the power of the laser, are set in step S902. A wafer is located at an inspection starting position in step S903. Then, the wafer is rotated and radially translated and a surface of the wafer is scanned with a laser beam in S905. Detection signals are generated upon the detection of foreign matter and defects in step S905. After the entire surface of the wafer has been inspected, the wafer is stopped and the inspecting operation is ended in step S906. A map or the like of information about the detected foreign matter and defects is provided in step S907 and the inspection procedure is ended in step S908.

Figure 10:
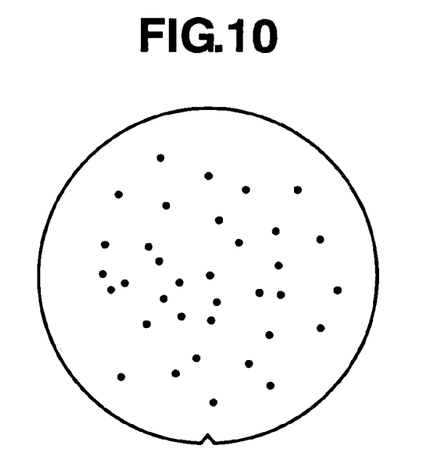
FIG. 10 is a diagram of a map of data which illustrates a method of displaying theoretical values of results of inspection.
Figure 11:
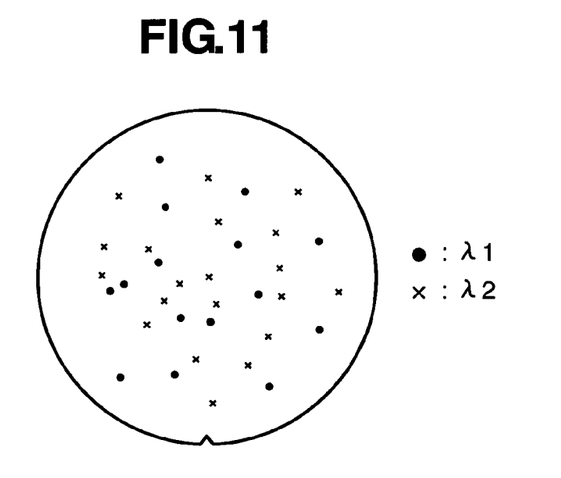
FIG. 11 is a diagram of a map of data which Illustrates a method of displaying results of inspection for wavelengths.
Figure 12:
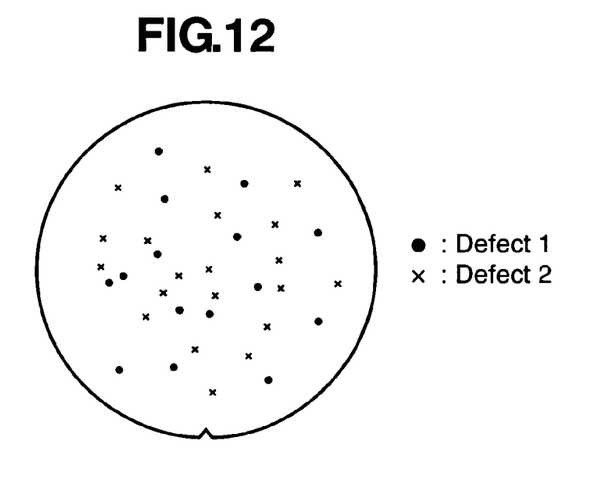
FIG. 12 is a diagram of a map of data which illustrates a method of displaying classified detects.

Maps of information about foreign matter and defects are shown by way of example in FIGS. 10, 11 and 12. FIG. 10 shows a map of data obtained by ORing information obtained by inspection. FIG. 11 shows a map of data obtained by the inspection apparatus shown in FIG. 8 and the inspection procedure shown in FIG. 9 for the wavelengths $\lambda 1$ and $\lambda$. FIG. 12 shows a map of data on individual types of defects.

The invention may be embodied in other specific forms without departing from the spirit or essential characteristics thereof. Therefore, the present embodiments are to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A defect detecting method comprising the steps of:
projecting a first laser beam having a wavelength in the range of 210 to 390 nm on a surface of a sample from a first direction inclined at an angle between 3° and 30° to the surface of the sample by projection of the first laser beam, the sample being a SOI wafer which has an oxide film layer and a SOI layer;
detecting light scattered from the surface of the sample by projection of the first laser beam;
projecting a second laser beam having a second wavelength in the range of 210 to 390 mm on the surface of the sample from a second direction inclined to the surface of the sample;
detecting light scattered from the surface of the sample by projection of the second laser beam; and
detecting defects including sizes below 0.1 μm formed on the surface of the sample by processing detection signals provided upon the detection of scattered light by projection of the first laser beam and the detection scattered light by projection of the second laser beam;

wherein in the step of projecting the first laser beam, said first laser beam is S polarized laser beam and a penetration depth of the first laser beam into the SOI layer formed on the surface of the sample is 10 nm or below in a condition when a reflectance of the first laser beam is 70% or above.

2. The defect detecting method according to claim 1, wherein in the step of detecting light by projection of the first laser beam, the scattered light reflected from the surface of the sample detected by a plurality of detectors set respectively at different detecting angles relative to the surface of the sample.

3. The defect detecting method according to claim 1, wherein the SOI wafer has a bulk Si, and the oxide film layer and the SOI layer are formed in layers on the bulk Si.

4. A defect detecting apparatus comprising:

a first laser beam projecting means for projecting a first laser beam having a first wavelength in the range of 210 to 390 nm on a surface of a sample from a first direction inclined at an angle between 3° and 30° to the surface of the sample, the sample being a SOI wafer which has an oxide film layer and a SOI layer;

a first scattered light detecting means for detecting light scattered from the surface of the sample caused by projection of the first laser beam from the first laser beam projecting means, and outputting a first detection signal;

a second laser beam projecting means for projecting a second laser beam having a second wavelength in the range of 210 to 390 nm on the surface of the sample from a second direction inclined to the surface of the sample;

a second scattered light detecting means for detecting scattered light reflected from the surface of the sample caused by projection of the second laser beam, and outputting a second detection signal; and a defect detecting means for detecting defects of sizes below 0.1 μm formed on the surface of the sample by processing outputs from the first scattered light detecting means and the second scattered light detecting means, wherein in said first laser beam projection means, said first laser beam in S polarized laser beam and a penetration depth of the first laser beam into the SOI layer formed on the surface of the sample is 10nm or below in a condition when a reflectance of the first laser beam is 70% or above.

5. The defect detecting apparatus according to claim 4, wherein the scattered light detecting means includes a plurality of detectors that receive scattered light reflected from the surface of the sample from a plurality of directions at different angles to the surface of the sample for detection.

6. The defect detecting apparatus according to claim 4, wherein the SOI wafer has a bulk Si, and the oxide film layer and the SOI layer are formed in layers in the bulk Si.

\* \* \* \* \*

UNITED STATES PATENT AND TRADEMARK OFFICE
CERTIFICATE OF CORRECTION

PATENT NO. : 7,643,139 B2  Page 1 of 1
APPLICATION NO. : 11/206209
DATED : January 5, 2010
INVENTOR(S) : Ohshima et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 391 days.

Signed and Sealed this

Twenty-first Day of December, 2010

David J. Kappos
*Director of the United States Patent and Trademark Office*